United States Patent [19]

Filli

[11] Patent Number: 5,036,835

[45] Date of Patent: Aug. 6, 1991

[54] ADJUSTABLE SLIDING LARYNGOSCOPE BLADE

[76] Inventor: Mesoud Filli, 74 Presidential Dr., Apt. 5, Quincy, Mass. 02169

[21] Appl. No.: 515,187

[22] Filed: Apr. 27, 1990

[51] Int. Cl.$^5$ .............................................. A61B 1/26
[52] U.S. Cl. ...................................... 128/11; 128/16
[58] Field of Search ................... 128/6, 10, 11, 15, 16, 128/17, 18, 20, 633, 634; 606/14

[56] References Cited

U.S. PATENT DOCUMENTS

| | | | |
|---|---|---|---|
| 2,433,705 | 12/1947 | Palmeter | 128/10 |
| 4,295,465 | 10/1981 | Racz et al. | 128/11 |
| 4,314,551 | 2/1982 | Kadell | 128/11 |

FOREIGN PATENT DOCUMENTS 2191949  12/1987  United Kingdom ................. 128/11

Primary Examiner—Stephen C. Pellegrino
Assistant Examiner—Glenn K. Dawson
Attorney, Agent, or Firm—H. Jay Spiegel

[57] ABSTRACT

Disclosed is an adjustable sliding laryngoscope including a blade portion including an adjustably attached spatula portion. The spatula is designed to be used as a tongue depresser to facilitate inspection of the pharynx and larynx or the insertion of anesthetic breathing tubes. The adjustable connection between the spatula portion and other portions of the blade portion is such that the length of the spatula may be adjusted to adjust for differing patient oral characteristics.

9 Claims, 4 Drawing Sheets

ADJUSTABLE SLIDING LARYNGOSCOPE BLADE

BACKGROUND OF THE INVENTION

The present invention relates to an adjustable sliding laryngoscope blade. In the prior art, laryngoscopes are known. Applicant is aware of U.S. Pat. Nos. 3,986,854 to Scribo, et al., 4,406,280 to Upsher, and 4,437,458 to Upsher. Each of these references teaches various aspects of a laryngoscope; however, none of these references teaches or suggests a laryngoscope having a base to which is adjustably attached the laryngoscope blade.

SUMMARY OF THE INVENTION

The present invention relates to an adjustable sliding laryngoscope blade. The present invention includes the following interrelated aspects and features:

(a) The inventive laryngoscope blade is intended, in use, to be associated with a laryngoscope device which may, in some aspects, be conventional. Such a device includes a handle to which the blade structure is attached, which handle includes a battery compartment, a switch, and electrical circuitry allowing electrical interconnection between batteries contained within the battery compartment and the light mounted on the blade.

(b) The blade is made in a generally Z-shaped cross-section having a spatula portion connected with a flange portion by a wall extending therebetween.

(c) The above-described flange portion, spatula portion and interconnecting wall are attached to a base comprising a neck section having coupling structure designed to couple with the handle as well as electrical connector structure designed to convey electrical current from the batteries contained in the handle to the light on the blade.

(d) In conventional prior art blade structures, the above-described components are normally formed as an integral sub-assembly of a laryngoscope device. In the present invention, to the contrary, the spatula portion of the blade is slidably mounted within a recess contained within the neck section so that the laryngoscope spatula portion may be extended outwardly from the neck section or may be moved therewithin. In this way, the degree of extension of the spatula portion of the blade may be adjusted.

(e) Such adjustment of the degree of extension of the spatula portion may be controlled by virtue of spaced depressions within the neck section recess and a spring-loaded detent mechanism on the spatula portion designed to selectively enter successive such recesses as the spatula portion is extended with respect to the rest of the blade structure.

(f) In a further aspect, structure is provided in the interconnection between the spatula portion and the rest of the blade structure to maintain electrical connection between the handle and the light regardless of the position of the spatula portion with respect to the rest of the blade structure.

Accordingly, it is a first object of the present invention to provide an improved adjustable sliding laryngoscope blade.

It is a further object of the present invention to provide such a device wherein the spatula portion of the blade is adjustable with respect to the rest of the blade structure thereof.

It is a still further object of the present invention to provide such a blade wherein illumination means is provided and electrical interconnection between the illumination means and its power source is maintained regardless of the position of the spatula portion.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 1:
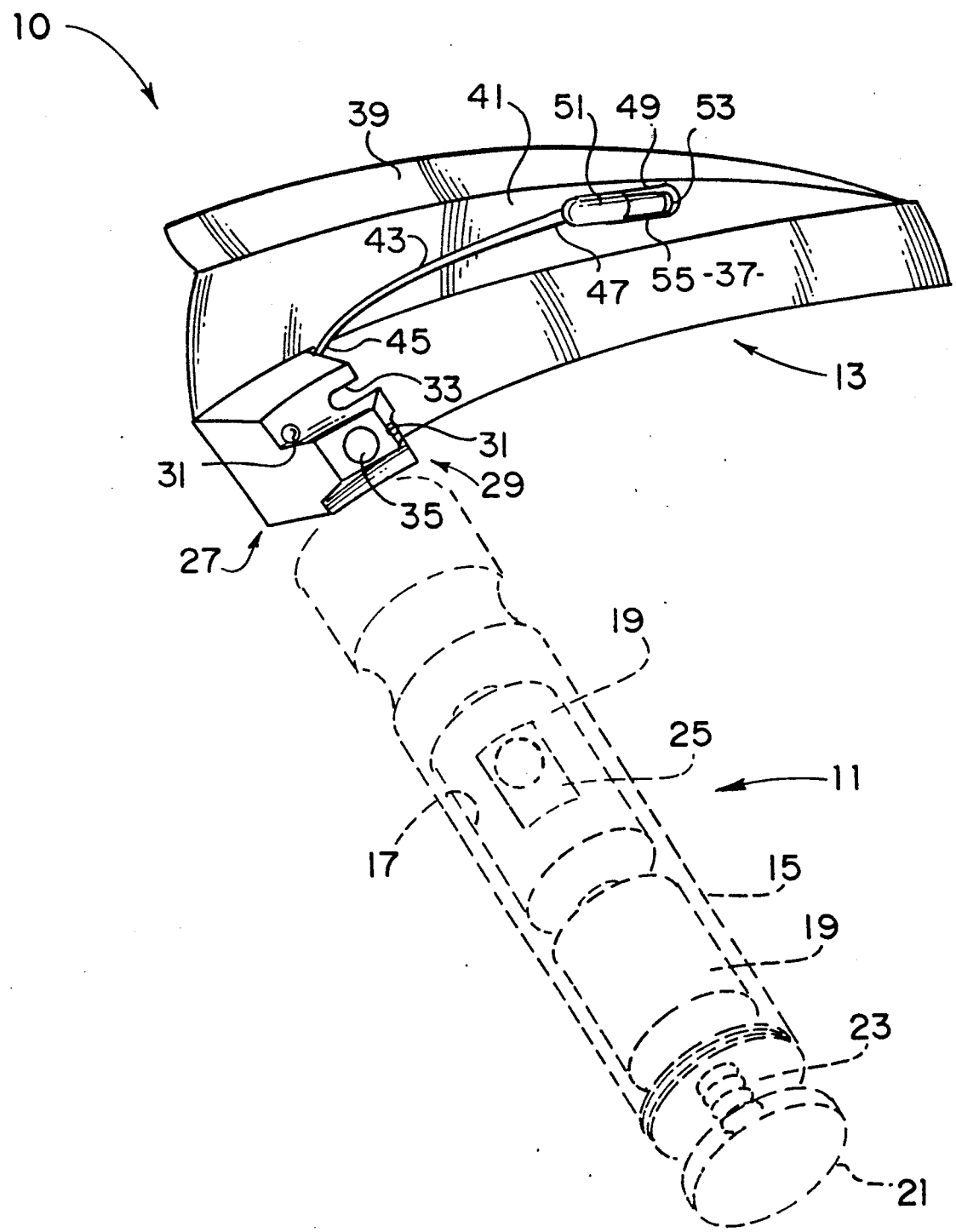
FIG. 1 shows a perspective view of a prior art laryngoscope, with certain parts broken-away to show detail.
Figure 2:
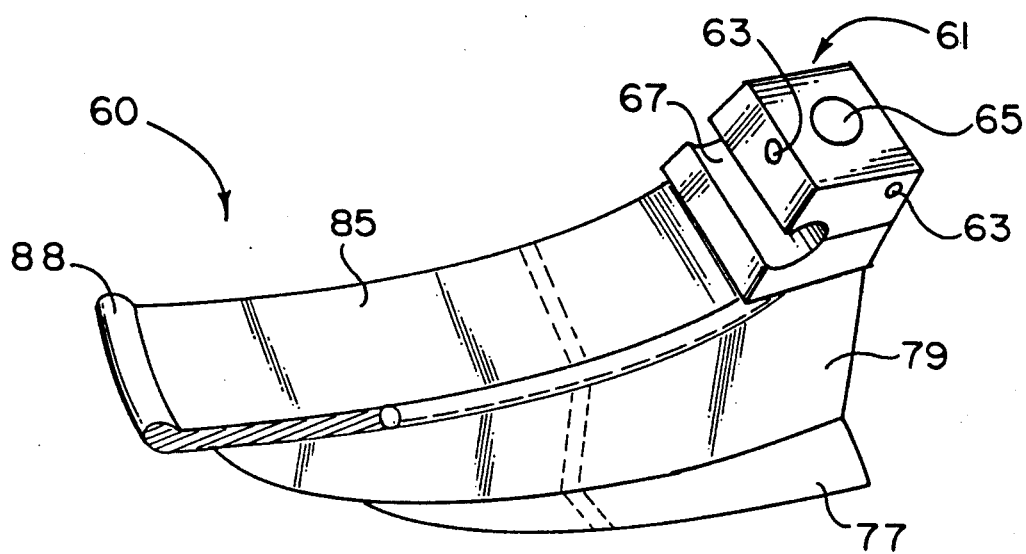
FIG. 2 shows a perspective view of a laryngoscope blade made in accordance with the teachings of the present invention.

With reference, first, to FIG. 1, a conventional prior art laryngoscope is generally designated by the reference numeral 10 and is seen to include a handle portion 11 and a blade portion 13. The handle portion 11 includes a generally cylindrical housing 15 having a hollow internal chamber 17 therein designed to receive batteries 19 with a cap 21 closing the chamber 17 and having a spring 23 designed to push the batteries 19 in the upward direction in the view of the figure. A switch mechanism 25 is provided and cooperates with internal circuitry (not shown) in the chamber 17 designed to electrically interconnect the batteries 19 with circuitry in the blade 13 as will be described in greater detail hereinafter.

The handle 11 includes a coupling mechanism 27 complimentary to a coupling mechanism 29 of the blade 13.

As described above, the blade 13 includes a coupling mechanism 29 which is complimentary to the coupling mechanism 27 of the handle 11 and allows the handle 11 and the blade 13 to be interconnected both mechanically and electrically. The coupling mechanism 29 includes detents 31 designed to engage corresponding recesses in the coupling mechanism 27 of the handle 11, includes a slot 33 designed to mesh with a protrusion in the coupling mechanism 27, and includes an electrical contact 35 designed to electrically interconnect with an electrical contact (not shown) in the coupling mechanism 27 of the handle 11.

With further regard to FIG. 1, the blade 13 includes a spatula portion 37, a flange portion 39, and a wall 41 interconnecting the spatula portion 37 and flange portion 39. As should be understood by those skilled in the art, the flange portion and the spatula portion are generally parallel to one another, while the wall 41 is generally mutually perpendicular to the flange portion 39 and the spatula portion 37. Since the flange portion 39 and the spatula portion 37 include some curvature, this parallel relationship is not completely the case; however, it is mentioned for purposes of understanding of the specific relationship between these elements.

A tube 43 connects at one end 45 with the coupling mechanism 29 and at another end 47 with illumination means 49 consisting of a socket 51 and a bulb 53. An electrical conductor (not shown) is carried within the tube 43 and connects at the end 45 via electrical circuitry (not shown) with the connector 35, and at the end 47 via electrical circuitry (not shown) with the socket 51 which electrically interconnects with the bulb 53. A slot 55 in the wall 41 is provided to allow the bulb to shine behind the wall 41 in the view of FIG. 1 and over the spatula portion 37 so that when a physician is examining the mouth and throat of a patient using the laryngoscope 10, the area of examination is appropriately illuminated.

Now, having generally described the prior art, reference is now made to FIGS. 2-9 wherein a preferred embodiment of the present invention is described.

For purposes of clarity, the preferred embodiment illustrated in FIGS. 2-9 does not include illustration of a handle portion such as that which is described with reference numeral 11 in FIG. 1. In this regard, it is intended that the coupler mechanism described with reference to FIGS. 2-9 correspond to the corresponding coupler mechanism 29 illustrated in FIG. 1 so that the inventive blade portion illustrated in FIGS. 2-9 may be equally effectively coupled to a handle portion such as that which is generally described with reference numeral 11 in FIG. 1.

The inventive blade portion illustrated in FIGS. 2-9 is generally designated by the reference numeral 60, and is seen to include a coupler mechanism 61 having detents 63 designed to enter corresponding recesses in the coupling mechanism of the corresponding handle (not shown), an electrical connector 65 designed to interconnect with a corresponding connector in the coupling mechanism of the handle (not shown), and a recess 67 designed to interconnect with a protrusion on the coupling mechanism of the handle portion (not shown).

Figure 5:
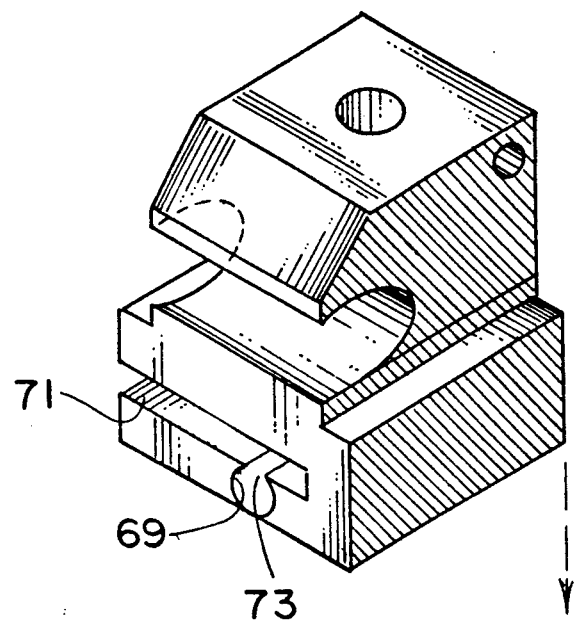
FIG. 5 shows a front perspective view of the neck section of the inventive laryngoscope blade.
Figure 6:
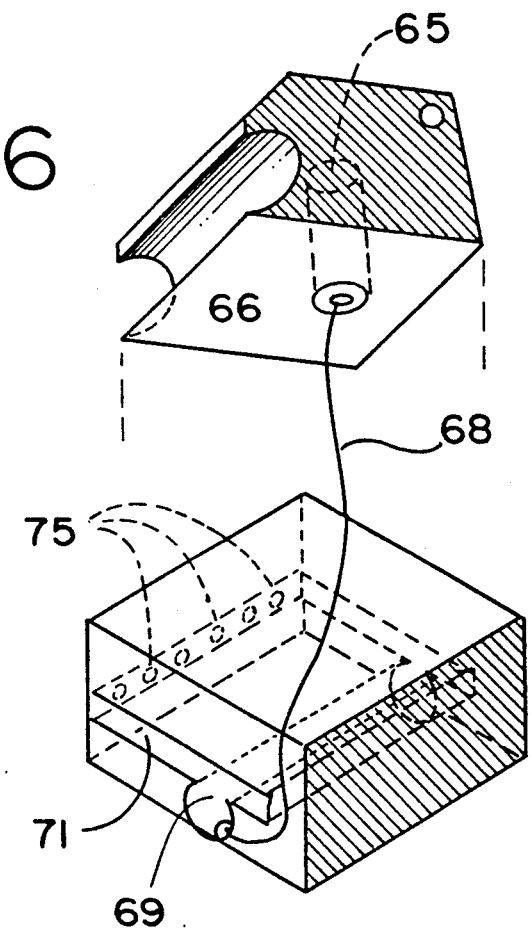
FIG. 6 shows an exploded perspective view of the structure shown in FIG. 5.
Figure 7:
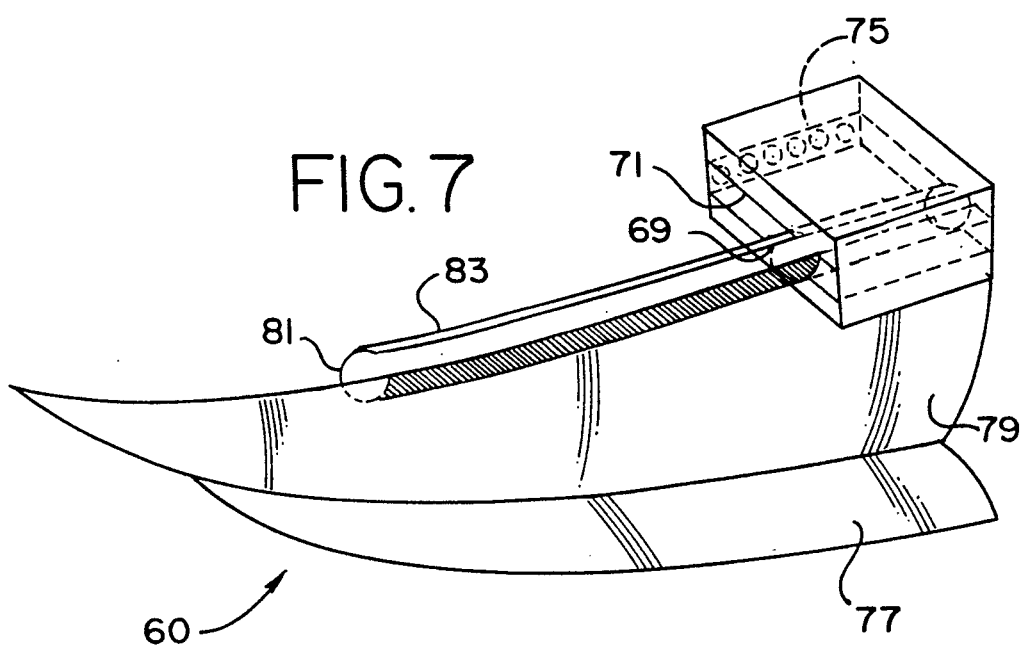
FIG. 7 shows the laryngoscope blade portion with the spatula portion thereof removed.

With reference to FIGS. 5-7, the coupling mechanism 61 is also seen to include a part cylindrical recess 69 interconnected with a thin elongated rectangular cubic recess 71 at an opening 73. As seen in FIGS. 6 and 7, one side of the recess 71 includes a plurality of depressions 75 therein for a purpose to be described in greater detail hereinafter.

With further reference to FIG. 7, it is seen that the inventive blade portion 60 includes a flange portion 77 and a wall portion 79 generally corresponding to the flange portion 37 and the wall portion 41 of the laryngoscope illustrated in FIG. 1. As seen in FIG. 7, however, an elongated cylindrical tube 81 is mounted at the top of the wall portion 79 and on one side wall thereof and extends outwardly from the recess 69 in the coupling mechanism 61, including an elongated slot 83 extending completely along its length.

Figure 3:
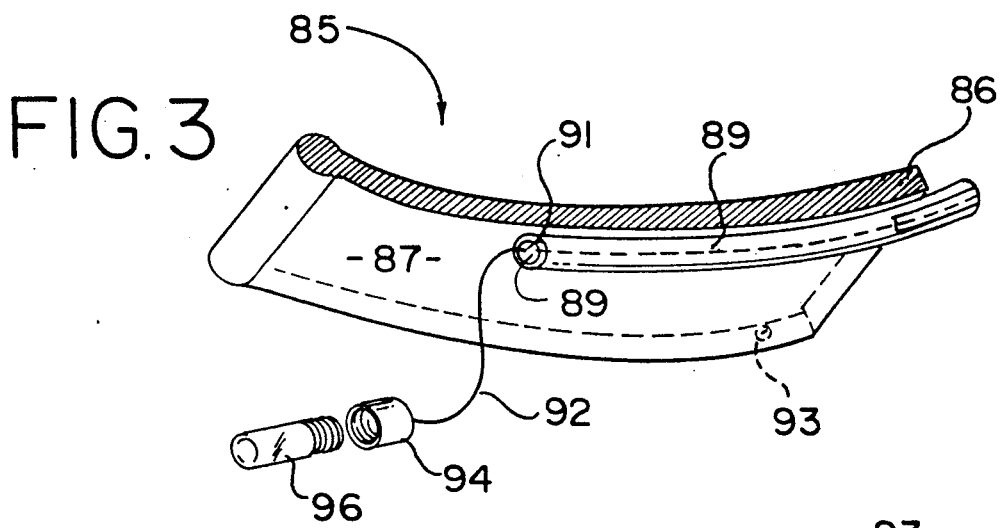
FIG. 3 shows a perspective view of the spatula portion of the inventive laryngoscope blade from a different angle from the view of FIG. 2.

With particular reference to FIG. 3, it is seen that the spatula portion 85 has mounted on an undersurface 87 thereof, an elongated cylindrical tube 89 having a passageway 91 therethrough. The outer diameter of the tube 89 is sized and configured to slidably move within the interior of the tube 81 of the wall portion 79 with the slot 83 in the tube 81 being oriented adjacent the spatula portion 85 surface 87.

Figure 4:
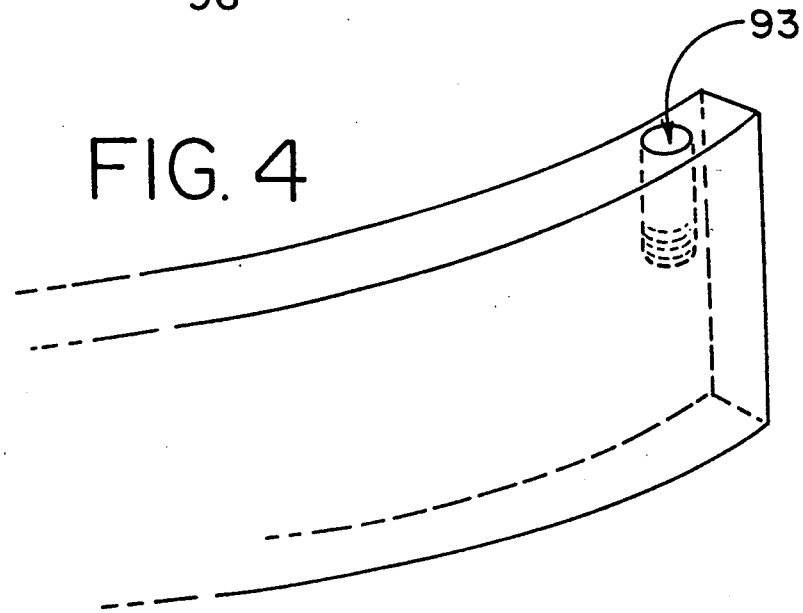
FIG. 4 shows a perspective view of an expanded portion of the structure shown in FIG. 3.

With reference to FIGS. 3 and 4, it is seen that a spring-loaded detent 93 is provided and is designed to engage in any one of the depressions 75 in the recess 71 as illustrated in FIG. 6 in particular to fix the position of the spatula portion 85.

With further reference to FIG. 6, it is seen that the connector 65 is electrically interconnected with the cylindrical recess 69 by virtue of an elongated electrical conductor 66 connected with a further electrical conductor 68. In a further aspect, the surfaces of the recess 69 as well as the entirety of the tube 89 are made of an electrically conductive material and the conductor 92 illustrated in FIG. 3 is interconnected with the electrically conductive cylinder 89 at one end and at another end with an electrical socket 94 designed to contain electrical bulb 96.

As should be understood with reference in particular to FIGS. 3, 6 and 7, the spatula portion 85 may be inserted within the recesses 69, 71 with a proximal end 86 of the spatula portion 85 being inserted within the recess 71 and with the cylindrical tube 89 being inserted within the cylindrical recess 69. As the spatula portion 85 is pushed into the recesses 69, 71, the detent 93 enters successive depressions 75 best seen in FIG. 6. As should be understood by those skilled in the art, interengagement of the detent 93 with one of the depressions 75 allows fixing of the relative position of extension of the spatula portion 85 with regard to the rest of the blade portion 60. In light of the electrical conductivity of the surfaces of the recess 69 and the entirety of the tube 89, electrical interconnection is maintained between the source of power in the handle section (not shown) and the bulb 96.

Figure 8:
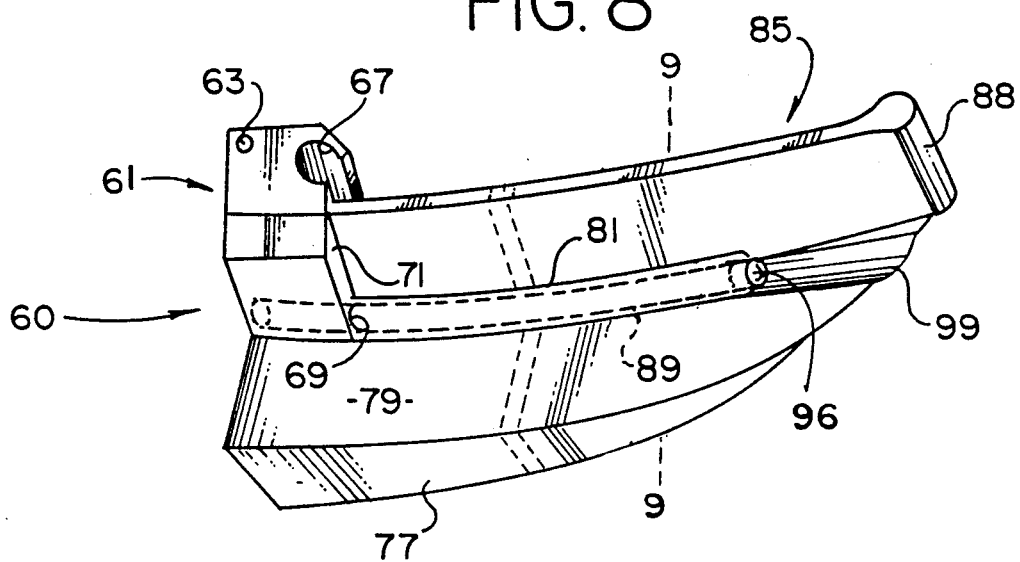
FIG. 8 shows a perspective view of the laryngoscope blade illustrated in FIG. 2, but upside down with respect thereto to show additional details.
Figure 9:
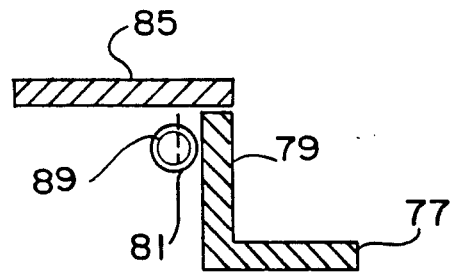
FIG. 9 shows a cross-sectional view along the line 9—9 of FIG. 8.

FIGS. 8 and 9 show the laryngoscope blade 60 in its assembled form, with FIG. 9 showing a cross-sectional view illustrating the relative positions of the spatula portion 85, the wall portion 79, and the interengaging cylinder 89 and tube 81. In FIG. 8, the wall portion 79 is seen to have a depression 99 therein designed to allow light from bulb 96 to emanate therepast.

With the above description in mind, the operation of the inventive improved adjustable sliding laryngoscope blade 60 should be self-evident. The physician may examine the interior regions of the mouth of the patient to determine, generally, the size of the tongue and the throat area. After such examination, the spatula portion 85 may be extended outwardly or may be further inserted inwardly with respect to the coupling mechanism 61 so that the distal end 88 of the spatula portion 85 is at a distance from the coupling mechanism 61 as desired, depending upon specific patient characteristics. The interaction between the detent 93 and one of the depressions 75 will maintain the relationship between the spatula portion 85 and the coupling mechanism 61 at the desired fixed configuration, while the electrical conductivity between the tube 81 and the cylinder 89 will maintain electrical power to the bulb 96 so that illumination of the area to be examined and viewed may be maintained.

This particular description of the present invention as illustrated in FIGS. 2-9 is to be considered as merely exemplary. Of course, other manners of interconnection of the spatula portion 85 with the rest of the blade 60 may be contemplated, and other means of maintaining electrical connection between the source of power in the handle (not shown) and the bulb 96 may be provided. Of course, the inventive laryngoscope may be made in two pieces, with the spatula portion 85 comprising one piece and the rest of the laryngoscope including the handle, the flange portion 77 and the wall portion 79 being made of an integral construction eliminating the need for the coupling mechanism 61 and a corresponding coupling mechanism on the handle portion. Furthermore, in lieu of the electrical conductivity maintained between the cylinder 89 the tube 81, alternatively, fiberoptics may be used to transmit light from the coupling mechanism 61 to a lens which would replace the bulb 96 so that transmission of light may be provided.

As to materials, the handle may be formed of a metal such as brass or aluminum, and the blade may be made of a similar material coated with a material such as, for example, chrome. To maintain conductivity between the cylinder 89 and the tube 81, these structures may be made of an electrically conductive material such as, for example, copper or silver.

As such, an invention has been described in terms of a preferred embodiment thereof which fulfills each and every one of the objects of the invention as set forth hereinabove, and provides a new and improved adjustable sliding laryngoscope which improves flexibility in such an instrument over the prior art. Use of the present invention eliminates the need for keeping in inventory a multiplicity of laryngoscope blade sections designed to be connected to a single handle. With the present invention, a single blade section may be used for patients of differing mouth configurations, thus eliminating the expense and inconvenience of having to keep in inventory such a plurality of different sized blade sections.

Of course, various changes, modifications and alterations in the teachings of the present invention may be contemplated by those skilled in the art without departing from the intended spirit and scope of the present invention. As such, it is intended that the present invention only be limited by the terms of the appended claims.

I claim:
1. In a laryngoscope having a handle means and a blade means, said blade means including a spatula portion, said spatula portion having a direction of elongation, the improvement comprising said spatula portion being linearly extendable generally in said direction of elongation relative to other portions of said blade means.
2. The invention of claim 1, wherein said blade means includes a recess, said spatula portion having a proximal end slidably received in said recess.
3. The invention of claim 2, wherein one of said recess or spatula portion proximal end includes a detent with the other of said recess or spatula portion proximal end including a plurality of depressions therein, said detent being engageable with any one of said depressions to fix the position of said spatula portion with respect to said recess.
4. The invention of claim 2, further including illumination means on said blade mean extending on one side of said spatula portion and electrically connected to a source of electrical power via said recess.
5. The invention of claim 4, wherein said recess comprises a flat portion connected to a cylindrical portion, said flat portion slidably receiving said spatula portion proximal end and said cylindrical portion slidably receiving a tube on said spatula portion, said tube carrying said illumination means.
6. The invention of claim 5, wherein said tube and a surface of said cylindrical portion engaging said tube are electrically conductive.
7. The invention of claim 4, wherein said illumination means comprises a light bulb.
8. The invention of claim 1, wherein said blade further includes a flange portion connected to said spatula portion via a wall portion.
9. The invention of claim 2, wherein said recess is located in a coupling mechanism of said blade mean.

* * * * *